US008152525B2

(12) United States Patent
Rossi, III

(10) Patent No.: US 8,152,525 B2
(45) Date of Patent: Apr. 10, 2012

(54) DENTAL PROSTHESIS REMOVAL TOOL

(76) Inventor: Henry D. Rossi, III, Port Washington, WI (US)

(*) Notice: Subject to any disclaimer, the term of this patent is extended or adjusted under 35 U.S.C. 154(b) by 212 days.

(21) Appl. No.: 12/543,523

(22) Filed: Aug. 19, 2009

(65) Prior Publication Data
US 2011/0045429 A1 Feb. 24, 2011

(51) Int. Cl.
A61C 13/00 (2006.01)
(52) U.S. Cl. ........................................ 433/167
(58) Field of Classification Search .................. 433/141, 433/215, 167
See application file for complete search history.

(56) References Cited

U.S. PATENT DOCUMENTS

| 2,602,998 | A | | 7/1952 | Sprague | |
|---|---|---|---|---|---|
| 2,831,480 | A | * | 4/1958 | Milano | 600/242 |
| 3,393,451 | A | | 7/1968 | Rasch | |
| 4,274,826 | A | | 6/1981 | Huey et al. | |
| 4,904,183 | A | | 2/1990 | Hannan et al. | |
| 5,032,082 | A | * | 7/1991 | Herrera | 433/141 |
| 5,092,770 | A | * | 3/1992 | Zakula | 433/172 |
| 5,217,371 | A | | 6/1993 | Lukase et al. | |
| 5,261,817 | A | | 11/1993 | Nack | |
| 5,378,151 | A | | 1/1995 | Lukase | |
| 6,015,293 | A | * | 1/2000 | Rimkus | 433/141 |
| 6,125,858 | A | * | 10/2000 | Button | 132/321 |
| 6,322,362 | B1 | * | 11/2001 | Holms | 433/143 |
| 6,755,815 | B2 | | 6/2004 | Schultz | |
| 7,011,517 | B2 | | 3/2006 | Nicozisis | |
| 7,381,054 | B1 | | 6/2008 | Polanowski | |
| 2003/0099918 | A1 | | 5/2003 | DeLuca | |
| 2006/0084032 | A1 | * | 4/2006 | Tipton et al. | 433/141 |
| 2006/0223029 | A1 | * | 10/2006 | Berger | 433/172 |
| 2009/0246732 | A1 | * | 10/2009 | Creasman et al. | 433/141 |
| 2010/0021863 | A1 | * | 1/2010 | Braman | 433/140 |

FOREIGN PATENT DOCUMENTS
KR 10-0289867 B1 5/2001
* cited by examiner

Primary Examiner — Cris L Rodriguez
Assistant Examiner — Eric Rosen
(74) Attorney, Agent, or Firm — Reinhart Boerner Van Deuren s.c.

(57) ABSTRACT

A dental prosthesis removal tool comprising a handle portion and a top portion, the top portion including a head portion and a beak portion. The beak portion is configured to engage both a maxillary dental prosthesis and a mandibular dental prosthesis without the tool needing to be reoriented. The dental prosthesis removal tool makes it possible for a dental prosthesis wearer to remove dental prostheses without the user placing his or her fingers inside of his or her mouth. The dental prosthesis removal tool also allows a denture wearer to remove dental prosthesis without bending, work hardening, or breaking metal clasps contained in some dental prostheses. The dental prosthesis removal tool further allows a denture wearer to more comfortably remove his or her dental prosthesis, promoting better patient compliance with maintenance procedures and oral hygiene.

5 Claims, 6 Drawing Sheets

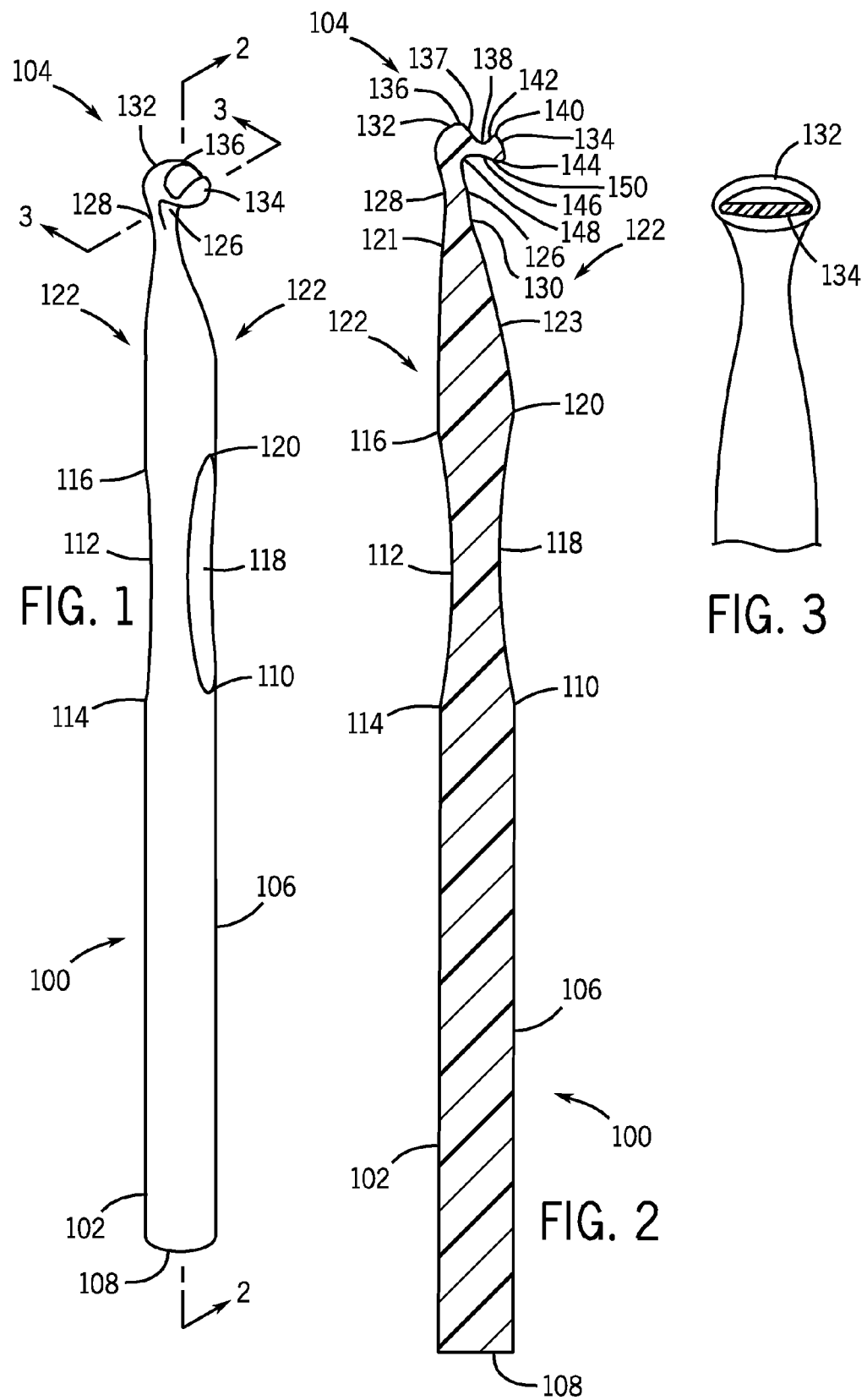

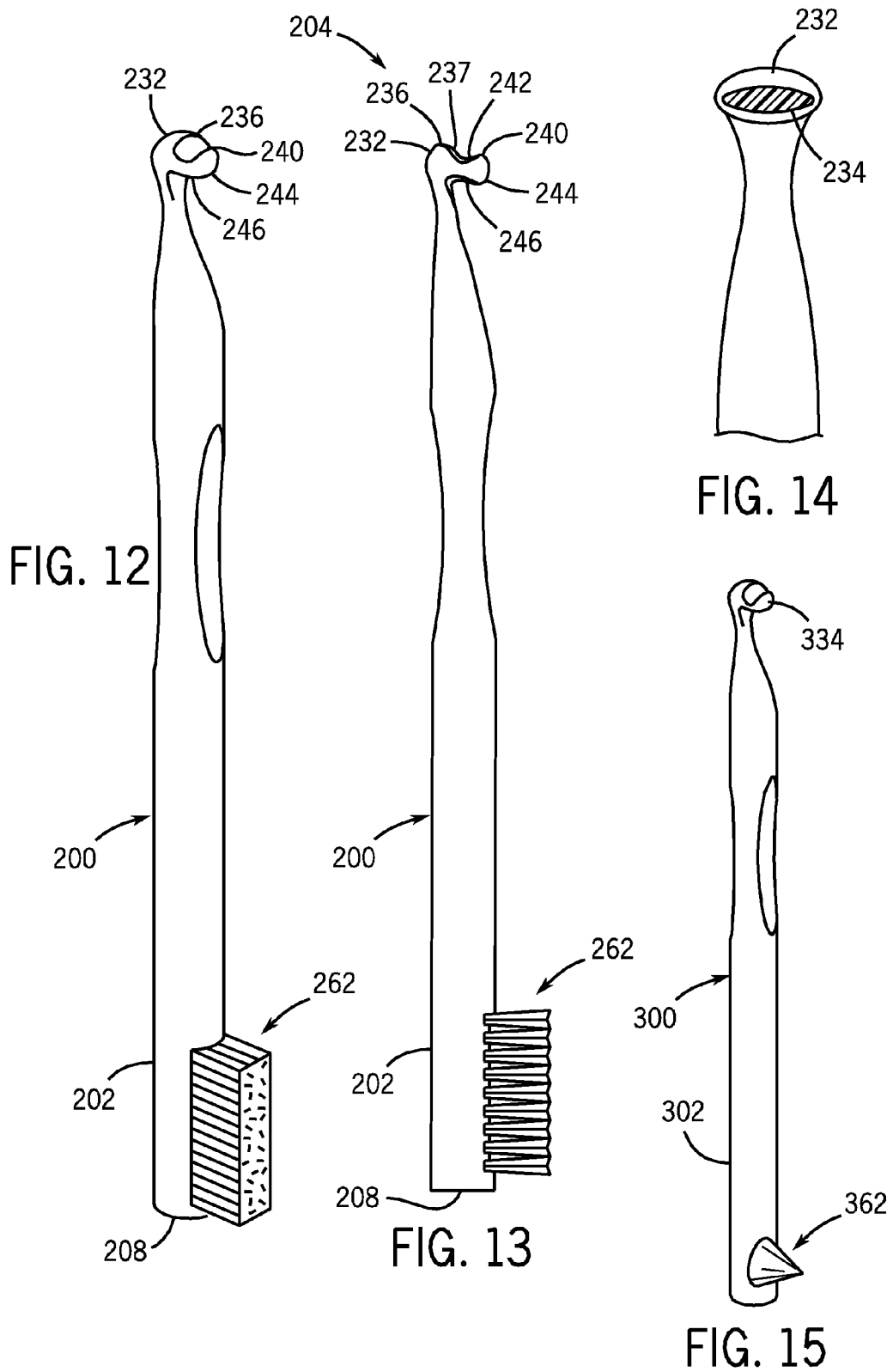

DENTAL PROSTHESIS REMOVAL TOOL

BACKGROUND OF THE INVENTION

Field of the Invention

The present invention relates generally to a dental prosthesis removal tool.

Removable oral prostheses or dentures are used to restore either full arch dentitions or partially edentulated dentitions. Complete full arch dentures are typically fabricated in acrylic. They rely upon a balanced combination of hard tissue and soft tissue support for retention. Removable partial dentures are fabricated with a chrome cobalt cast metal framework supporting acrylic saddles in the edentulated areas. They gain direct mechanical retention from clasping other teeth in the dental arch. Overdentures are acrylic prostheses similar to complete dentures, but are retained by precision attachments, typically milled snap mechanical retainers of various designs providing variable retention force. The precision attachments are placed on endodontically treated retained roots or dental implants.

In the past, proper denture removal techniques included placing one's fingers along the acrylic flanges and pushing in the direction opposite the dental ridge. Unfortunately, because fingers are poorly suited to function as dental removal tools, denture wearers were forced to use their fingernails to pull on the acrylic portion of the dentures, or in the case of removable partial dentures, to pull on the cast metal clasps to dislodge the dentures. When this procedure is employed, over time these metal clasps may become bent or work hardened and have a tendency to break. Overdentures retained by precision attachments can be even more difficult to remove, requiring up to five pounds of force to dislodge them, making them difficult to remove with a tool as poorly suited for removal as a finger, especially for those with limited manual dexterity. Because of the difficulty of removing dentures, dental practitioners and clinicians were limited in how much retention force they could design the denture to provide.

Thus, it would be advantageous for denture wearers to be able to remove their dentures without the need to place their fingers inside of their mouths.

It would also be advantageous for those denture wearers with limited manual dexterity to be able to remove their dentures more easily and, again, without placing their fingers in their mouths.

It would be advantageous for dental practitioners and clinicians not to be constrained by the difficulty of removing dentures when designing the amount of retention force that the denture will provide.

It would also be advantageous for a denture to be constructed of suitable material such that the denture be configured for customization or alteration by a dental professional to better fit a specific situation.

Further, it would be advantageous for denture wearers to have a way to remove dentures that would limit damage to the dentures including reducing or eliminating bending, work hardening, or breaking of the metal clasps.

It would also be advantageous for denture wearers to have a denture removal tool with no moving parts to break or wear out.

It would further be advantageous for denture wearers to have a more comfortable way to remove their dental prostheses, which would encourage better patient compliance with maintenance procedures, as well as improved oral hygiene.

The dental prosthesis removal tool of the present invention must also be of a construction which is both durable and long lasting, and it should also require little or no maintenance to be provided by the user throughout its operating lifetime. In order to enhance the market appeal of the dental prosthesis removal tool of the present invention, the tool should also be of relatively inexpensive construction to thereby afford it the broadest possible market. Finally, it is also an objective that all of the aforesaid advantages and objectives of the dental prosthesis removal tool of the present invention be achieved without incurring any substantial relative disadvantage.

SUMMARY OF THE INVENTION

An embodiment of the dental prosthesis removal tool of the present invention is described below. The dental prosthesis removal tool is for removing both the maxillary and mandibular dental prostheses of a user. The tool includes a handle portion, a top portion, and a transition portion coupling the handle portion to the top portion. The top portion also includes a head portion coupled to a beak portion. The beak portion also includes a maxillary dental prosthesis engaging portion and a mandibular dental prosthesis engaging portion. The beak portion is configured to engage and remove both the maxillary dental prosthesis and the mandibular dental prosthesis without the user reorienting the dental prosthesis relative to either a jaw or a hand of the user.

The dental prosthesis removal tool may be made of injection molded plastic or other materials. The dental prosthesis removal tool may contain a toothbrush or a rubber tip stimulator.

The dental prosthesis removal tool is able to remove overdentures retained by snap-fitting to snap-fit anchors implanted in the jaw of the denture wearer, as well as dentures retained by good fit or denture paste.

The dental prosthesis removal tool of the present invention is of a construction which is both durable and long lasting, and it should also require little or no maintenance to be provided by the user throughout its operating lifetime. The dental prosthesis removal tool of the present invention is also of relatively inexpensive construction to enhance its market appeal and to thereby afford it the broadest possible market. Finally, the dental prosthesis removal tool of the present invention achieves all of the aforesaid advantages and objectives without incurring any substantial relative disadvantage.

DESCRIPTION OF THE DRAWINGS

These and other advantages of the present invention are best understood with reference to the drawings, in which:

FIG. 1 is an isometric view of an embodiment of the dental prosthesis removal tool of the present invention;

FIG. 2 is a side cross-sectional view of the dental prosthesis removal tool illustrated in FIG. 1;

FIG. 3 is a front partial cross-sectional view of the dental prosthesis removal tool illustrated in FIGS. 1 and 2;

FIG. 12 is an isometric view of a second embodiment of the dental prosthesis removal tool of the present invention having a differently shaped head and a handle that includes a toothbrush;

FIG. 13 is a side plan view of the dental prosthesis removal tool of FIG. 12;

FIG. 14 is a front partial cross-sectional view of the second embodiment of the dental prosthesis removal tool of FIGS. 12 and 13; and FIG. 15 is an isometric view of a third embodiment of the dental prosthesis removal tool of the present invention having a rubber tip stimulator coupled to the handle of the dental prosthesis removal tool.

DETAILED DESCRIPTION OF THE EXEMPLARY EMBODIMENTS

Figure 4:
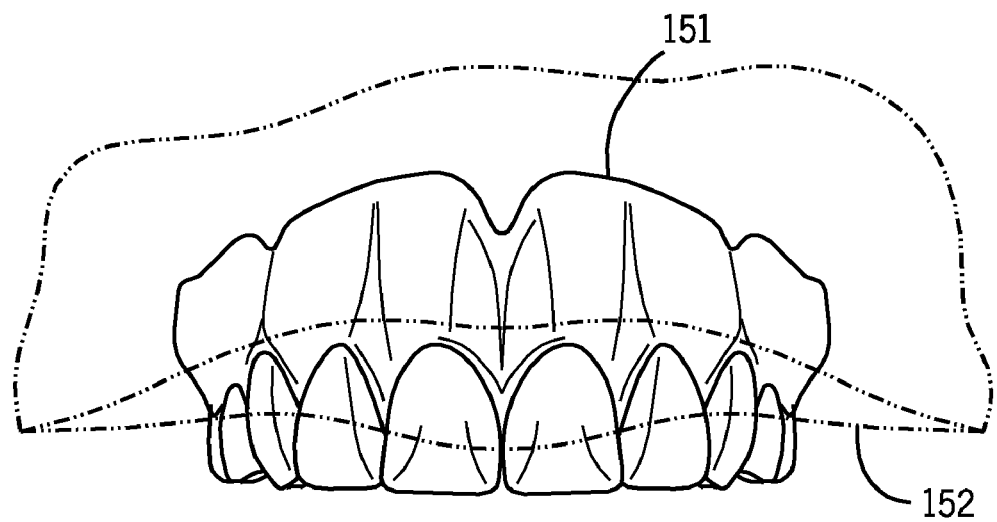
FIG. 4 is an isometric front view of a maxillary denture located inside a denture wearer's mouth.

An exemplary dental prosthesis removal tool 100 is illustrated in FIG. 1. The dental prosthesis removal tool 100 may be formed from injection molded plastic in a process that is much like the manufacture of a toothbrush. Other methods of making the dental prosthesis removal tool 100 may instead be used, including making the dental prosthesis removal tool 100 in a single pull mold. Other materials may be used as well, including various metals and composites, as well as combinations thereof. These are mentioned only as examples and are not meant to limit the invention as various other materials could instead be used.

As will be further described below, the dental prosthesis removal tool 100 is designed to be used by a denture wearer to assist in easily removing either or both maxillary and mandibular dentures. It is intended that the user be able to hold the handle of the dental prosthesis removal tool 100 and be able to remove both maxillary and mandibular dentures without the user changing his or her grip on the handle or reconfiguring the orientation of the dental prosthesis removal tool 100 in relation to the user's hand or mouth. In one embodiment of the present invention, the dental prosthesis removal tool 100 is intended to be used to remove dentures by engaging the dentures at or near the front of the mouth; however, other embodiments could instead removing dentures by engaging the dentures at other locations.

In FIG. 1 an embodiment of the dental prosthesis removal tool 100 comprises a handle portion 102 and a top portion 104. The handle portion 102 can be of any shape that is conducive to gripping by a user. In the embodiment of the dental prosthesis removal tool 100 shown, the handle portion 102 is of a generally cylindrical shape. Many configurations of the handle portion 102 are envisioned, including a slender toothbrush style as well as larger bulbous styles allowing for ease of gripping, as well as many other sizes and styles.

In the embodiment shown in FIG. 1, the handle portion 102 includes a hand portion 106, which extends from the bottom end 108 of the dental prosthesis removal tool 100 to a junction 110, a finger portion 112, which extends from a junction 114 to a junction 116, and a thumb portion 118, which extends from the junction 110 to a junction 120. The finger portion 112 is generally an arcuate depression in the handle portion 102 that is configured to receive a user's finger or fingers and provide better leverage and grip for the user's finger or fingers. Likewise, the thumb portion 118 is an arcuate depression in the handle portion 102, approximately on the opposite side of the handle portion 102 from the finger portion 112, configured to receive a user's thumb and to provide better leverage and grip for the user's thumb. These arcuate depressions can be of various depths and slopes configured to accommodate all different sizes and shapes of hands. Other grip-assisting methods and configurations are also envisioned.

In one embodiment of the dental prosthesis removal tool 100, the handle portion 102 is coupled to the top portion 104 by way of a transition portion 122. With reference to FIGS. 1 and 2, the transition portion 122 has two surfaces, illustrated best in FIG. 2, including a finger portion side surface 121 and a thumb portion side surface 123. The transition portion 122 begins at the junction 120 on the thumb portion 118 side of the dental prosthesis removal tool 100 and ends at the junction 126, while on the finger portion 112 side of the dental prosthesis removal tool 100 the transition portion 122 begins at the junction 116 and continues to the junction 128. The finger portion side surface 121 slopes gradually inward from the junction 116 to the junction 128, while the thumb portion side surface 123 slopes at a substantially greater angle inward from the junction 120 to the junction 130, and then the angle inward decreases from the junction 130 to the junction 126. The greater angle inward portion from the junction 120 to the junction 130 allows a denture wearer to position the dental prosthesis removal tool 100 into operable contact with dentures (not shown in FIGS. 1 and 2) more easily and to allow better access around the denture wearers lip to a mandibular denture. The transition portion 122 terminates at the top portion 104 of the dental prosthesis removal tool 100.

Continuing with reference to FIGS. 1 and 2, the top portion 104 of one embodiment of the dental prosthesis removal tool 100 comprises a head portion 132 and a beak portion 134 extending generally laterally from the head portion 132. The head portion 132 is a generally rounded arc that terminates at a junction 136, and the beak portion 134 begins at this junction 136. With reference primarily to FIG. 2, a generally non-arcuate attachment portion 137 slopes sharply downwardly from the head portion 132 towards the handle portion 102 and extends from the junction 136 to a low point at the junction 138. A mandibular engagement portion 142 extends from the attachment portion 137 at the junction 138. The mandibular engagement portion 142 extends from the junction 138 to the junction 140, and is generally shaped to facilitate engagement with the mandibular denture. The mandibular engagement portion 142 is generally concave, and extends up to a local maximum at the junction 140, creating a hooked shape that is well-suited to engage a manibular denture, and, as will be discussed further below, maintain engagement with the manibular denture when the force necessary to remove the denture is applied in a direction away from the mandible by the denture wearer.

The beak portion 134 continues from the junction 140 and generally hooks down and around slightly back toward the head portion 132 to reach a junction 144, at which point a maxillary denture engagement portion 146 begins which extends from the junction 144 to a junction 148 at the head portion 132. The maxillary denture engagement portion 146 is generally concave, but from the junction 144 to a junction 150 the maxillary denture engagement portion 146 has a greater angle of concavity than it does from the junction 150 to the junction 148. This greater angle of concavity allows the maxillary denture engagement portion 146 to be well-suited to engage the top of a maxillary denture and maintain engagement as a denture wearer applies force in a direction towards the mandible to remove the maxillary denture.

With reference to FIG. 3, in one embodiment of the present invention, the head portion 132 preferably has a greater radius than the beak portion 134, which can help to facilitate denture removal, though many other configurations are envisioned.

FIG. 4 illustrates a maxillary denture inside of a denture wearer's mouth. Typically, to remove a maxillary denture, a denture wearer would need to provide a force on an upper edge 151 of the denture using a finger. However, because of the configuration of a denture wearer's upper lip 152, it is difficult to position a finger in operable contact with the upper edge 151.

Figure 5:
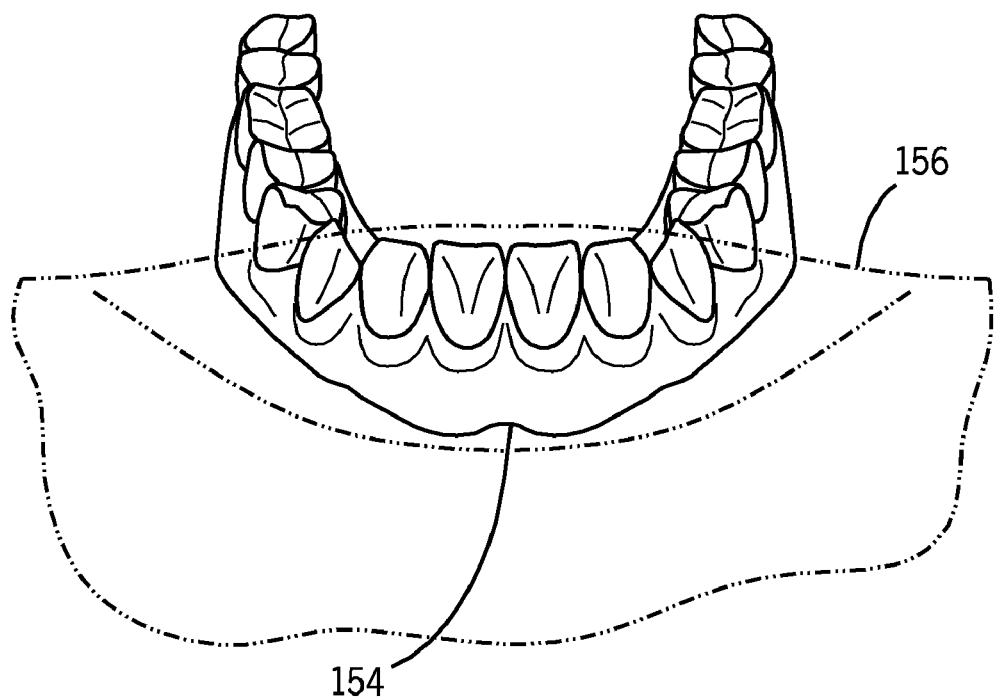
FIG. 5 is an isometric front view of a mandibular denture located inside a denture wearer's mouth.

Similarly, FIG. 5 shows a mandibular denture with a lower edge 154. A denture wearer typically must position a finger in operable contact with lower edge 154 to remove the mandibular denture, but again the configuration of a denture wearer's lower lip 156 makes this difficult and uncomfortable.

Figure 6:
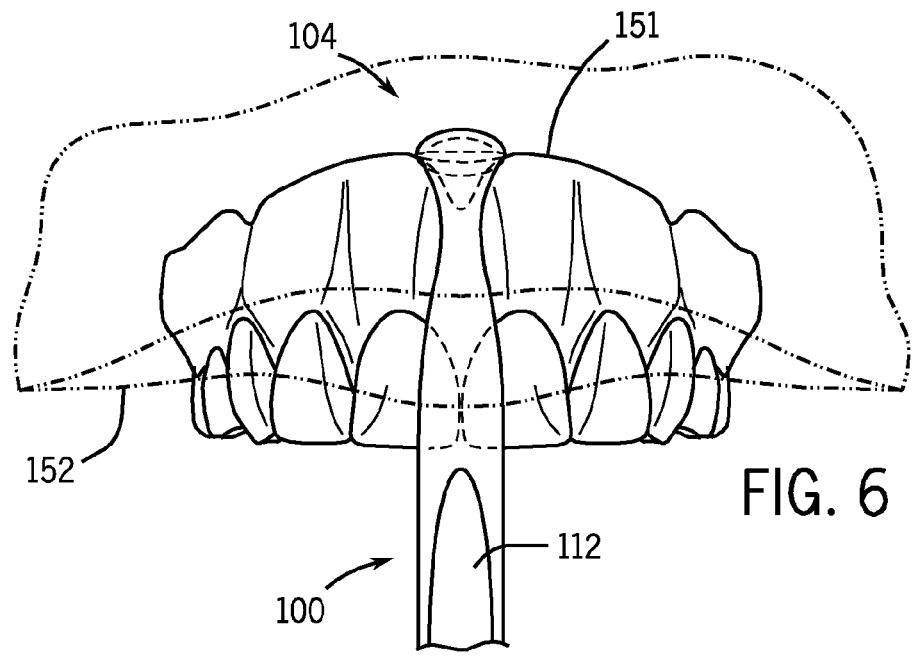
FIG. 6 is an isometric front view of the dental prosthesis removal tool of FIGS. 1-3 engaging the maxillary denture of FIG. 4 located inside a denture wearer's mouth.

FIG. 6 illustrates the dental prosthesis removal tool 100 in engagement with the upper edge 151 of a maxillary denture inside of denture wearer's mouth. The dental prosthesis removal tool 100 is well-suited to reach beneath the upper lip 152 of a denture wearer and be easily placed in operative engagement with a maxillary denture of a denture wearer.

Figure 7:
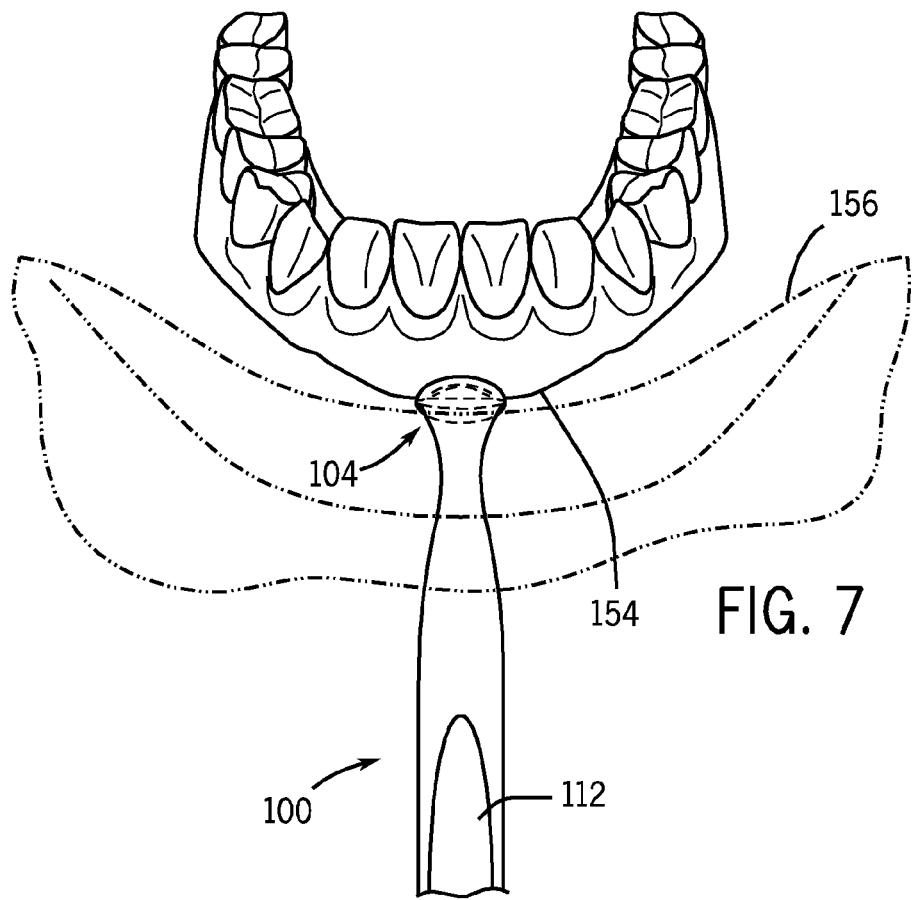
FIG. 7 is an isometric front view of the dental prosthesis removal tool of FIGS. 1-3 and 6 engaging the mandibular denture of FIG. 4 located inside a denture wearer's mouth.

Similarly, FIG. 7 illustrates the dental prosthesis removal tool 100 in operative engagement with the lower edge 154 of a mandibular denture inside of a denture wearer's mouth. The dental prosthesis removal tool is well-suited to reach over the lower lip 156 of a denture wearer and easily operably engage the lower edge 154 of a denture wearer's mandibular denture.

The finger portion 112 is illustrated in both FIGS. 6 and 7 as being oriented on the side of the dental prosthesis removal tool 100 opposite the denture wearer's upper 152 and lower 156 lips, while the thumb portion 118 (not shown in FIGS> 6 and 7) is located on the side of the dental prosthesis removal tool 100 facing the denture wearer's upper 152 and lower 156 lips. Further, the top portion 104 of the dental prosthesis removal tool 100 is proximate to the denture (maxillary or mandibular) being removed, while the bottom end 108 is distal from the denture (maxillary or mandibular) being removed. The orientation of the dental prosthesis removal tool 100 shown in FIGS. 6 and 7 is maintained when removing either of the two different dentures, so a denture wearer is able to remove both the maxillary and mandibular dentures without changing the orientation of the dental prosthesis removal tool 100 or the position of the denture wearer's hand on the dental prosthesis removal tool 100.

Figure 8:
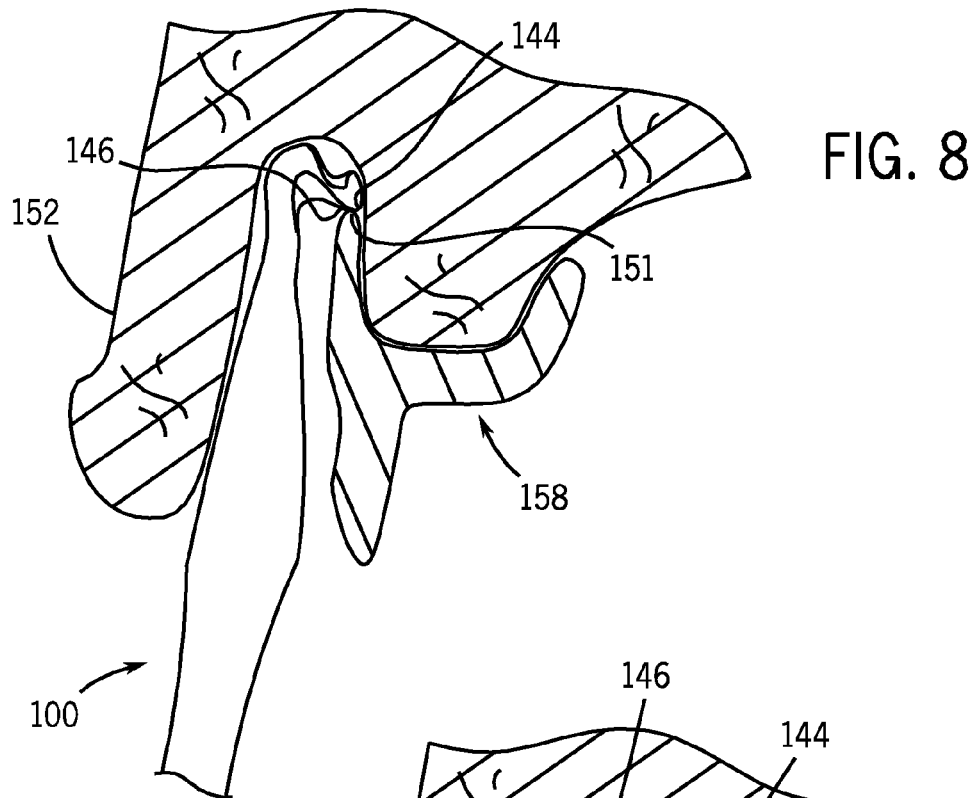
FIG. 8 is an isometric, close-up, side view of the dental prosthesis removal tool of FIGS. 1-3, 6, and 7 engaging a partial cross-section of a maxillary denture in engagement with a denture wearer's mouth in preparation for denture removal.
Figure 9:
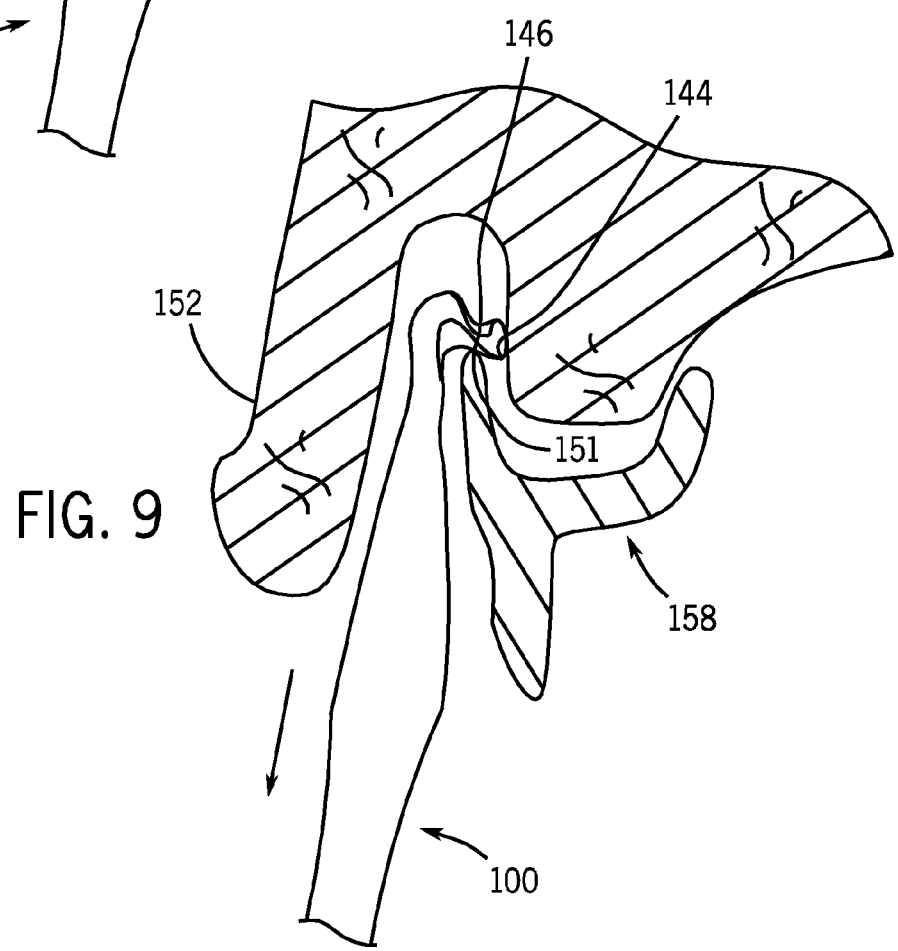
FIG. 9 is an isometric, close-up, side view of the dental prosthesis removal tool of FIGS. 1-3 and 6-8 removing a partial cross-section of a maxillary denture from engagement with a denture wearer's mouth using a downward pulling motion away from the maxillary jaw.

FIGS. 8 and 9 illustrate a close-up, partial cross-sectional view of the dental prosthesis removal tool 100 in operative engagement with a maxillary denture 158, with the upper edge 151 located inside of the mouth of a denture wearer. The junction 144 and the maxillary denture engagement portion 146 engage the upper edge 151, and because of the generally concave shape of the junction 144 and maxillary denture engagement portion 146, the dental prosthesis removal tool 100 is held in operative engagement with the maxillary denture when a pulling force is applied by a denture wearer in the direction of the mandible as illustrated in FIG. 9. Preferably, the dental prosthesis removal tool 100 remains in operative contact with the maxillary denture 158 throughout disengagement of the maxillary denture 158, pulling the maxillary denture 158 away from engagement with the denture wearer's mouth.

Figure 10:
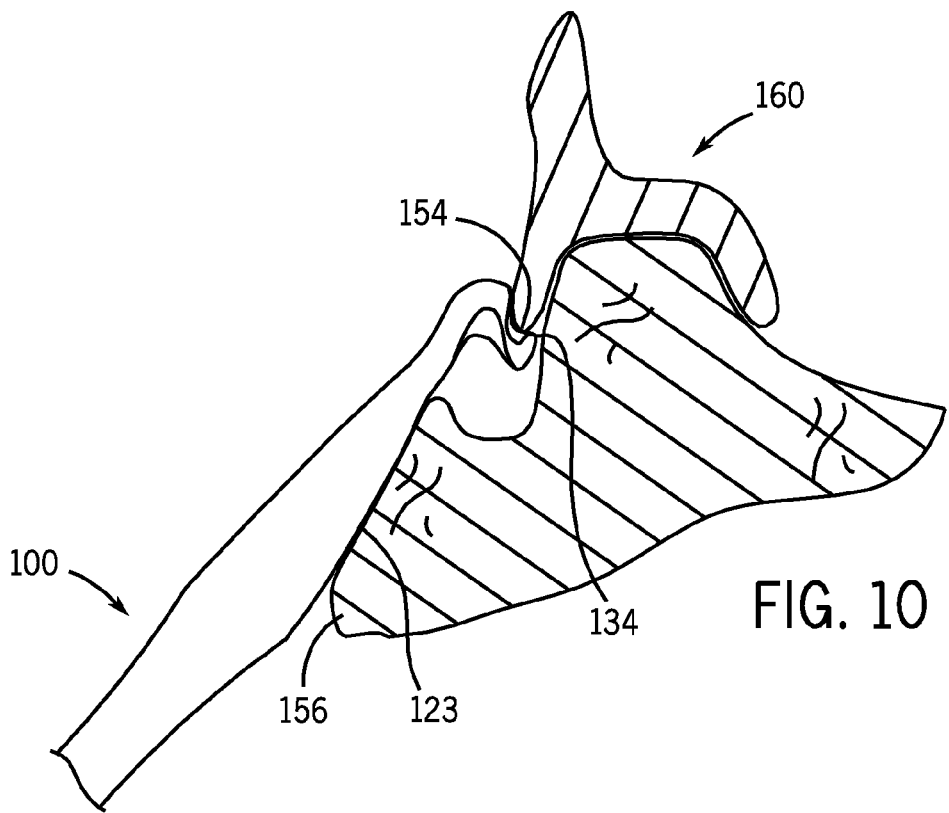
FIG. 10 is an isometric, close-up, side view of the dental prosthesis removal tool of FIGS. 1-3 and 6-9 engaging a partial cross-section of a mandibular denture in engagement with a denture wearer's mouth in preparation for denture removal.
Figure 11:
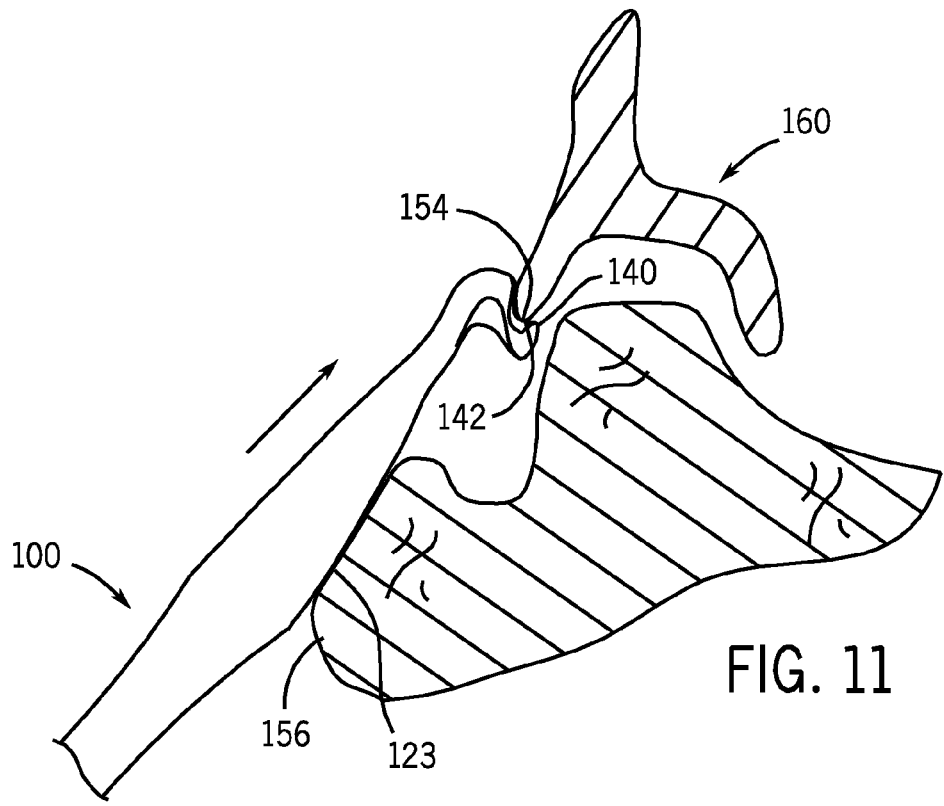
FIG. 11 is an isometric, close-up, side view of the dental prosthesis removal tool of FIGS. 1-3 and 6-10 removing a partial cross-section of a mandibular denture from engagement with a denture wearer's mouth using an upward pushing motion away from the mandibular jaw.

FIGS. 10 and 11 illustrate a close-up, partial cross-sectional view of the dental prosthesis removal tool 100 in operative engagement with a mandibular denture 160, with the lower edge 154 located inside of the mouth of a denture wearer. The junction 140 and the mandibular engagement portion 142 engage the lower edge 154 of the mandibular denture 160, and because of the generally concave shape of the junction 140 and mandibular engagement portion 142, the dental prosthesis removal tool 100 is held in operative engagement with the mandibular denture when a pushing force is applied by a denture wearer in a direction away from the mandible as illustrated in FIG. 11. Preferably the dental prosthesis removal tool 100 remains in operative contact with the mandibular denture 160 throughout disengagement of the mandibular denture 160, lifting the mandibular denture 160 away from engagement with the denture wearer's mouth.

FIGS. 10 and 11 also illustrate the need for the steep slope of the thumb portion side surface 123. Because of the angle at which the dental prosthesis removal tool 100 must be inserted into a denture wearer's mouth to make operative contact with the lower edge 154 of the mandibular denture 160, as well as the configuration of the denture wearer's lower lip 156, this steep slope of the thumb portion side surface 123 allows the dental prosthesis removal tool 100 to reach over and around the lower lip 156 to engage the lower edge 154 of the denture wearer's mandibular denture 160.

FIGS. 8-11 illustrate dentures retained in the mouth through good fit or denture paste. However, these merely two examples of the type of dentures that the dental prosthesis removal tool of the present invention could operate on and remove. The dental prosthesis removal tool of the present invention is also capable of removing dentures that are retained through snap mating with snap anchors implanted in the maxillary and mandibular jaws. The dental prosthesis removal tool of the present invention would engage with and remove dentures retained by snap mating in the same way as it removes dentures as illustrated in FIGS. 8-11. The dental prosthesis removal tool is particularly well-suited to engage and remove these snap mating dentures for all the reasons described above.

FIG. 12 illustrates a second embodiment of a dental prosthesis removal tool 200. The dental prosthesis removal tool 200 differs from the dental prosthesis removal tool 100 in several significant ways. Elements of the dental prosthesis removal tool 200 that are similar to elements of the dental prosthesis removal tool 100 are given similar reference numerals, but in the 200 series instead of in the 100 series. First, with reference to a top portion 204, a head portion 232 does not extend to as high a local maximum as does the corresponding head portion 132 in the dental prosthesis removal tool 100. Also, an attachment portion 237 that attaches the head portion 232 to a mandibular engagement portion 242 has a much more gentle slope than the corresponding attachment portion 137 in the dental prosthesis removal tool 100. The mandibular engagement portion 242 also has a more gentle slope that engagement portion 142 in the dental prosthesis removal tool 100. A junction 240 which ends the mandibular engagement portion 242 is subsequently a lower local maximum than is the corresponding junction 140 in the dental prosthesis removal tool 100. A junction 244 also does not extend as far out from a beak portion 234 as the corresponding junction 144 in the dental prosthesis removal tool 100, giving a maxillary engagement portion 246 less of a hooked end. This is only one of many other possible alternate configurations of the top portion 204 of the dental prosthesis removal tool of the present invention. Many other slopes and configurations are envisioned to suit many different mouths and many different needs. The configuration of the second embodiment 200 is shown only as an example of such other possible configurations and is not meant to limit the present invention in any way.

Finally, a handle portion 202 proximate a bottom end 208 has bristles that are coupled to and extend outwardly from the handle portion 202 to form a toothbrush 262. The toothbrush 262 may be on any side of the handle portion 202. In FIG. 12, the toothbrush 262 is shown as extending from the same side as does the beak portion 234.

FIG. 14 illustrates a partial cross-section of the second embodiment 200 of the present invention.

FIG. 15 illustrates a third embodiment of a dental prosthesis removal tool 300 having a beak portion 334. A rubber tip stimulator 362 is coupled to and extends outwardly from a handle portion 302. It is envisioned that the rubber tip stimulator 362 could extend outwardly from the handle portion 302 in any direction. FIG. 15 illustrates the rubber tip stimulator 362 extending from the handle portion 302 in the same direction as does the beak portion 334.

For purposes of this disclosure, "dentures" includes overdentures, removable partial dentures, partially edentulated dentitions, complete full arch dentures, and all other types of dentures that one skilled in the art would recognize as being equivalent to or substitutes for the dentures listed above that are capable of being removed using the dental prosthesis removal tool of the present invention.

For purposes of this disclosure, the term "coupled" means the mechanical joining of two components directly or indirectly to one another. Such joining may be stationary in nature or moveable in nature. Such joining may be achieved with the two components and any additional intermediate members being integrally formed as a single unitary body with one another or the two components and any such additional member being attached to one another. Such adjoining may be permanent in nature or alternatively be removable or releasable in nature.

The dental prosthesis removal tool of the present invention is of a construction which is both durable and long lasting, and it should also require little or no maintenance to be provided by the user throughout its operating lifetime. The dental prosthesis removal tool of the present invention is also of relatively inexpensive construction to enhance its market appeal and to thereby afford it the broadest possible market. Finally, the dental prosthesis removal tool of the present invention achieves all of the aforesaid advantages and objectives without incurring any substantial relative disadvantage.

Although the foregoing description of the dental prosthesis removal tool and method of the present invention has been shown and described with reference to particular embodiments and applications thereof; it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the dental prosthesis removal tool and method of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the dental prosthesis removal tool and method of the present invention as determined by the appended claims when interpreted in accordance with the breadth to which they are fairly, legally, and equitably entitled.

What is claimed is:

1. A method of removing a maxillary dental prosthesis and a mandibular dental prosthesis comprising:
providing a member having a handle portion at a first end thereof, a top portion at a second opposite end thereof, and a transition portion located intermediate said handle portion and said top portion, said top portion having a head portion located at an end of said top portion distal from said transition portion;
providing said head portion with a beak portion extending generally laterally from said head portion, said beak portion comprising a maxillary dental prosthesis engaging portion located on a first side of said beak portion and a mandibular dental prosthesis engaging portion located on a second side of said beak portion that is opposite said first side of said beak portion; and
removing the maxillary dental prosthesis by orienting the member in a first orientation relative to a user, engaging the maxillary dental prosthesis with the maxillary dental prosthesis engaging portion of said beak portion and pulling said handle downwardly away from a maxillary jaw; and
removing the mandibular dental prosthesis, while maintaining the member in the first orientation relative to the user, by engaging the mandibular dental prosthesis with the mandibular dental prosthesis engaging portion on said beak portion and pushing said handle upwardly away from a mandibular jaw.

2. The method of removing a maxillary dental prosthesis and a mandibular dental prosthesis of claim 1, wherein the member is made of injection molded plastic material.

3. The method of removing a maxillary dental prosthesis and a mandibular dental prosthesis of claim 1, wherein said handle portion further comprises a toothbrush.

4. The method of removing a maxillary dental prosthesis and a mandibular dental prosthesis of claim 1, wherein said handle portion further comprises a rubber tip stimulator.

5. The method of removing a maxillary dental prosthesis and a mandibular dental prosthesis of claim 1, wherein at least one of the maxillary dental prosthesis and the mandibular dental prosthesis is an overdenture, retained by a snap-fit to a snap anchor.

* * * * *

UNITED STATES PATENT AND TRADEMARK OFFICE
CERTIFICATE OF CORRECTION

| | | |
|---|---|---|
| PATENT NO. | : 8,152,525 B2 | |
| APPLICATION NO. | : 12/543523 | |
| DATED | : April 10, 2012 | |
| INVENTOR(S) | : Henry D. Rossi, III | |

It is certified that error appears in the above-identified patent and that said Letters Patent is hereby corrected as shown below:

On the Title Page, Item (57) In the Abstract:

"The dental prosthesis removal tool also allows a denture wearer to remove dental prosthesis without bending, work hardening, or breaking metal clasps contained in some dental prostheses." should read --The dental prosthesis removal tool also allows a denture wearer to remove dental prostheses without bending, work hardening, or breaking metal clasps contained in some dental prostheses.--.

Signed and Sealed this
Eighth Day of May, 2012

David J. Kappos
*Director of the United States Patent and Trademark Office*